United States Patent [19]
McLean et al.

[11] Patent Number: 6,033,410
[45] Date of Patent: Mar. 7, 2000

[54] ORTHOPAEDIC INSTRUMENTATION

[75] Inventors: Christopher McLean; Robert Hodorek; Mike LaLonde; Ron Donkers, all of Warsaw; Mark Heldreth, Mentone, all of Ind.

[73] Assignee: Bristol-Myers Squibb Company, New York, N.Y.

[21] Appl. No.: 09/224,903

[22] Filed: Jan. 4, 1999

[51] Int. Cl.$^7$ .................................................. A61B 17/00
[52] U.S. Cl. .................................................. 606/88; 606/87
[58] Field of Search ........................................ 606/87, 88

[56] References Cited

U.S. PATENT DOCUMENTS 5,417,694   5/1995   Marik et al. .............................. 606/88

*Primary Examiner*—Michael Buiz
*Assistant Examiner*—Julian W. Woo
*Attorney, Agent, or Firm*—Todd A. Dawson

[57] ABSTRACT

Orthopaedic instrumentation used for preparing a distal end of a femur during an orthopaedic revision surgery includes a cutting guide block with a medial side, a lateral side and an anterior cutting guide surface. The medial side and the lateral side each have a notch therein. An anterior flange is removably attached to the cutting guide block and positioned adjacent to the anterior cutting guide surface. The anterior flange includes a pair of arms which are respectively disposed within the medial side notch and the lateral side notch.

19 Claims, 3 Drawing Sheets

ORTHOPAEDIC INSTRUMENTATION

BACKGROUND OF THE INVENTION

1. Field of the Invention

The present invention relates to instrumentation used in orthopaedic surgery, and, more particularly, to instrumentation used to prepare bone for receiving a prosthesis.

2. Description of the Related Art

In an orthopaedic surgery to replace part or all of a bone joint with a prosthetic implant, a portion of the implant receiving bone is prepared to closely match the mating surfaces of the implant. During an orthopaedic surgery to replace a knee joint, the distal end of the femur is prepared to accommodate a femoral knee component and the proximal end of the tibia is prepared to accommodate a tibial component.

During a revision surgery, an orthopaedic implant which was previously implanted into a bone is removed and a new implant is implanted into the bone. Because of differences between implants used during a primary surgery and a revision surgery and/or because of changes in the shape of the previously prepared bone, it is usually necessary to reshape the end of the bone to receive the implant which is implanted during the revision surgery.

What is needed in the art is orthopaedic instrumentation which allows the distal end of a femur to be quickly and accurately sized and shaped for reception of an implant during a revision surgery.

SUMMARY OF THE INVENTION

The present invention provides orthopaedic instrumentation with an anterior flange which is removably attachable with a selected one of a plurality of cutting guide blocks.

The invention comprises, in one form thereof, orthopaedic instrumentation used for preparing a distal end of a femur during an orthopaedic revision surgery. A cutting guide block includes a medial side, a lateral side and an anterior cutting guide surface. The medial side and the lateral side each have a notch therein. An anterior flange is removably attached to the cutting guide block and positioned adjacent to the anterior cutting guide surface. The anterior flange includes a pair of arms which are respectively disposed within the medial side notch and the lateral side notch.

An advantage of the present invention is that the anterior flange can be used with one of a plurality of different width cutting guide blocks.

Another advantage is that the cutting guide block includes two abutment surfaces which can be selectively placed against the distal end of the femur for use with a fight or left distal femur.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 1:
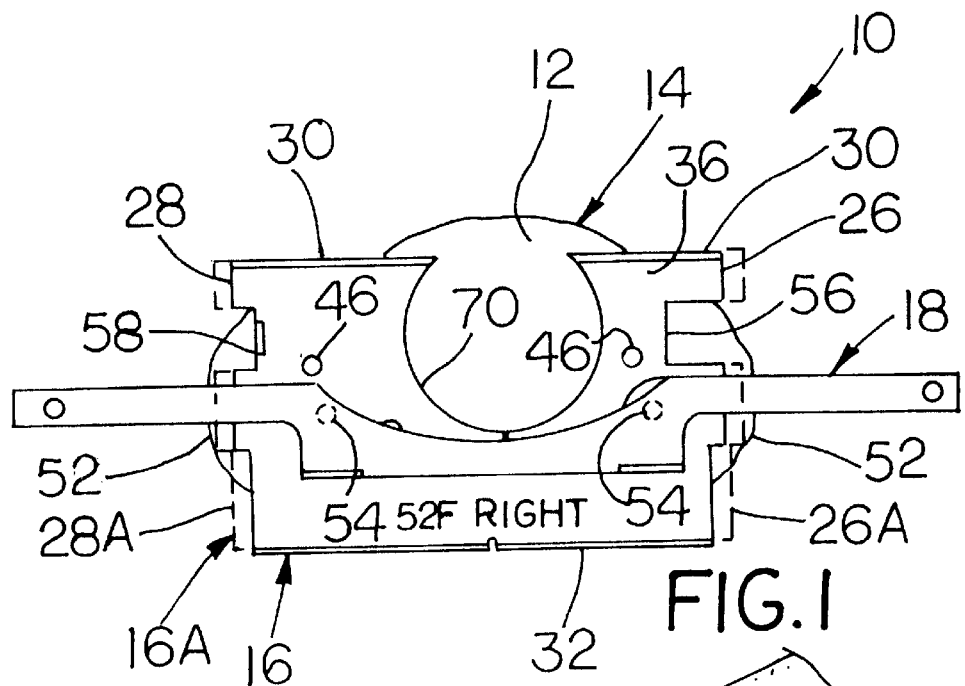
FIG. 1 is a front view of orthopaedic instrumentation including an embodiment of a cutting guide block and rotational alignment guide of the present invention, shown in relation to the distal end of a femur.
Figure 2:
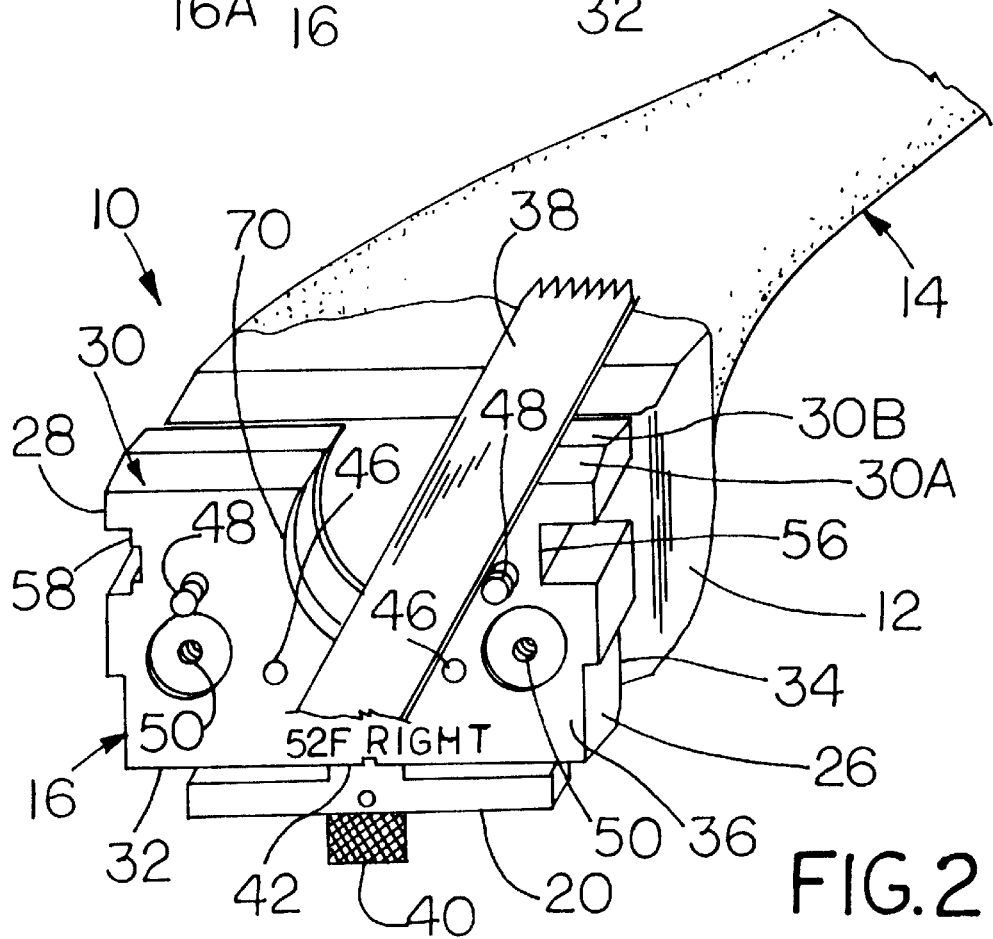
FIG. 2 is a perspective view of the cutting guide block of FIG. 1 pinned to the distal end of a femur, with a posterior saw guide attached to the cutting guide block and a saw blade against the anterior cutting guide surface.
Figure 3:
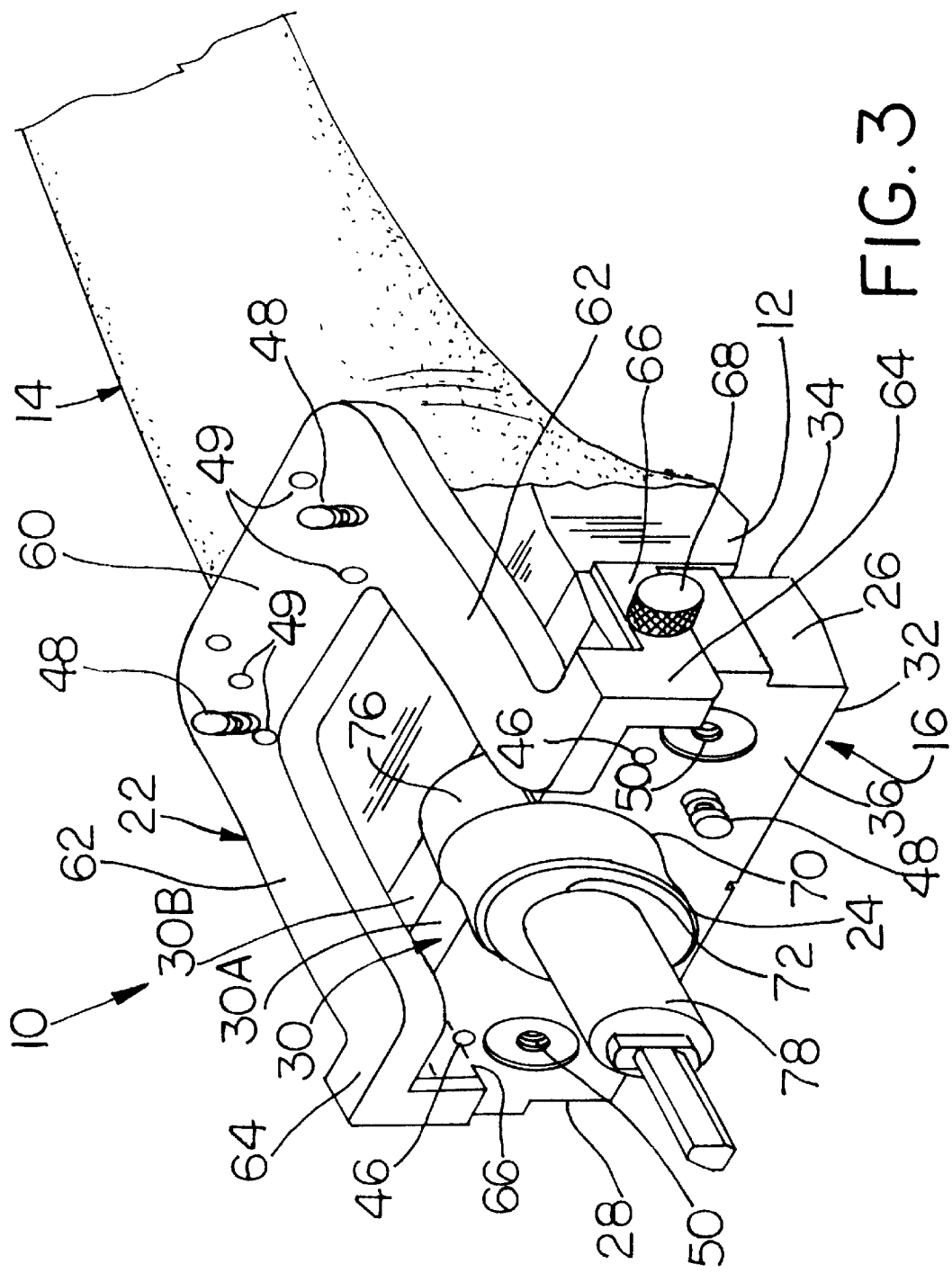
FIG. 3 is a perspective view of the cutting guide block attached with an embodiment of an anterior flange and guide bushing of the present invention, with a drill bit within the guide bushing.

Referring now to the drawings, and more particularly to FIGS. 1–3, there is shown orthopaedic instrumentation 10 which is used for preparing a distal end 12 of a femur 14 during an orthopaedic revision surgery. Orthopaedic instrumentation 10 generally includes a cutting guide block 16, rotational alignment guide 18, posterior saw guide 20, anterior flange 22 and bushing 24.

Cutting guide block 16 includes a medial side 26, a lateral side 28, an anterior cutting guide surface 30, a posterior cutting guide surface 32 and a pair of abutment surfaces 34 and 36. Cutting guide block 16 has a width which extends between medial side 26 and lateral side 28. The width of cutting guide block 16 is used as a sizing guide to determine the size of an implant to be implanted within femur 14. For example, one of a plurality of cutting block 16, each having a different width extending between medial side 26 and lateral side 28, may be used as sizing guides to determine the width of an implant which is implanted within femur 14. As the width of cutting guide block 16 varies from one block to another, the general shape of medial side 26 and lateral side 28 remains the same (as indicated by phantom lines in FIG. 1).

Cutting guide block 16 is configured to be used with either a right hand femur 14 or a left hand femur (not shown). In the embodiment shown, cutting guide block 16 is positioned such that abutment surface 34 lies adjacent to the distal end of right hand femur 14 (as indicated by the visual indicia "RIGHT" adjacent to posterior cutting guide surface 32). If cutting guide block 16 is used in conjunction with a left hand femur (not shown), abutment surface 36 is placed against the distal end of the left hand femur and the visual indicia on abutment surface 34 (not visible) provides a visual verification to the surgeon that the correct abutment surface 34 or 36 has been placed against the distal end of the femur.

Anterior cutting guide surface 30 is a segmented surface with two cutting guide surfaces 30A and 30B which abut each other at an obtuse angle. Cutting guide surface 30A is used for guiding a saw blade 38 when cutting guide block 16 is used in conjunction with a right femur 14 (FIG. 2); and cutting guide surface 30B is used to guide a saw blade 38 when cutting guide block 16 is used with a left hand femur (not shown).

Posterior cutting guide surface 32 is a segmented surface including two abutting surfaces disposed at an obtuse angle relative to each other. Posterior saw guide 20 is attached to posterior cutting guide surface 32 of cutting guide block 16 using a threaded thumb screw 40 with a threaded projection which is received within a corresponding threaded hole in posterior cutting guide surface 32. A keying arrangement 42 between posterior saw guide 20 and posterior cutting guide surface 32 ensures proper alignment and interconnection between posterior saw guide 20 and cutting guide block 16. A pair of guide slots 44 defined between posterior saw guide 20 and posterior cutting guide surface 32 allow saw blade 38 to be received therein for shaping a posterior side of femur 14.

Cutting guide block 16 also includes a plurality of pin holes 46 for receiving bone pins 48 which are used to affix cutting guide block 16 to a distal end of femur 14. Recessed threaded holes 50 provide threaded interconnection with other orthopaedic instrumentation (not shown).

Rotational alignment guide 18 is in the form of an epicondylar alignment guide which allows cutting guide block 16 to be aligned relative to epicondyles 52 of femur 14. Epicondylar alignment guide 18 includes two projecting pins 54 with an outside diameter which is slightly less than the inside diameter of recessed threaded holes 50.

Pins 54 may thus be projected into holes 50 such that epicondylar alignment guide 18 is detachably connected with cutting guide block 16.

Medial side 26 and lateral side 28 each include a respective notch 56 and 58 therein. Notches 56 and 58 allow cutting guide block 16 to be removably attached with anterior flange 22, as will be described in more detail hereinafter. Regardless of the width of a selected cutting guide block 16, the distance between notches 56 and 58 remains the same so that a selected cutting guide block 16 having a width corresponding to an implant to be implanted within femur 14 may modularly be attached with the same anterior flange 22. This reduces the number of parts required during orthopaedic surgery using orthopaedic instrumentation 10. For example, referring to FIGS. 1 and 4, it may observed that cutting guide block 16 has a width extending between medial side 26 and lateral side 28 which corresponds to a size F implant to be implanted within femur 14. A cutting guide block 16A (shown in phantom lines in FIGS. 1 and 4) has a width extending between medial side 26A and lateral side 28A which is larger than the width of cutting guide block 16. Nonetheless, the distance between notches 56 and 58 remains the same, regardless of the overall width of cutting guide block 16 or 16A. In this manner, anterior flange 22 may be connected with any selected cutting guide block having a width corresponding to the particular size of an implant to be implanted within femur 14.

Anterior flange 22 is removably attached to cutting guide block 16 and is positioned adjacent to anterior cutting guide surface 30. Anterior flange 22 includes a U-Shaped plate 60 with two depending legs 62. Each leg 62 is connected via an interconnecting portion 64 with a depending arm 66. Arms 66 are respectively disposed within medial side notch 56 and lateral side notch 58. A thumb screw 68 connected with an arm 66 on the medial side is threadingly received within arm 66. Threading the shaft of thumb screw 68 into a corresponding threaded opening in arm 66 causes thumb screw 68 to exert a compressive force against notch 56, thereby interconnecting anterior flange 22 with cutting guide block 16. Loosening thumb screw 68 allows arms 66 to be slid from within notches 56 and 58 for detachment between anterior flange 22 and cutting guide block 16.

Figure 5:
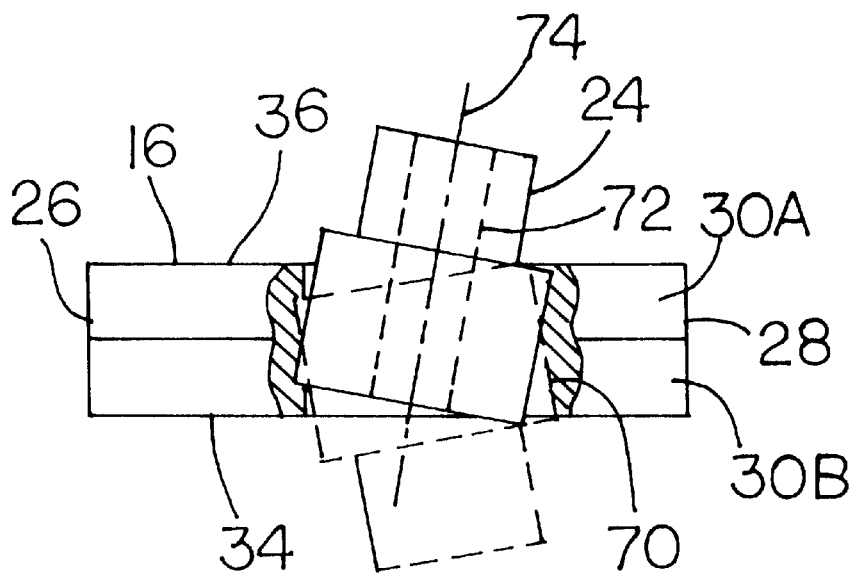
FIG. 5 is a fragmentary sectional view of the cutting guide block and guide bushing of FIG. 3.

Opening 70 extending between abutment surfaces 34 and 36 receives a bushing 24 therein. Bushing 24 includes an opening 72 having a selected diameter which is configured to receive an intramedullary rod, reamer or drill bit. Opening 72 is concentrically disposed about a longitudinal axis 74 of bushing 24. In the embodiment shown in FIG. 3, bushing 24 has an opening 72 which is sized to receive a drill bit 78 therein. Opening 70 in cutting guide block 16 includes multiple abutting surfaces (FIG. 5) which allow bushing 24 to be received within cutting guide block 16 at a predetermined angle, relative to an abutment surface 36 or 34. As shown in FIG. 5, bushing 24 may be inserted into cutting guide block 16 from the side facing abutment surface 36 and is held in the position shown during use. In the event that cutting guide block 16 is used with a left hand femur such that abutment surface 36 is placed against the distal end of the femur, bushing 24 may be inserted from the side facing abutment surface 34 (as shown in phantom lines in FIG. 5) and is held in place at the angle shown. Thus, as cutting guide block 16 is flipped over from one orientation to another for use with either a left hand or a right hand femur, bushing 24 is automatically held at a predetermined angular orientation upon insertion into cutting block 16.

Bushing 24, in the embodiment shown, includes a projecting key 76 which prevents rotational movement between bushing 24 and cutting guide block 16 when bushing 24 is inserted into cutting guide block 16. Other keying arrangements are of course also possible.

Figure 4:
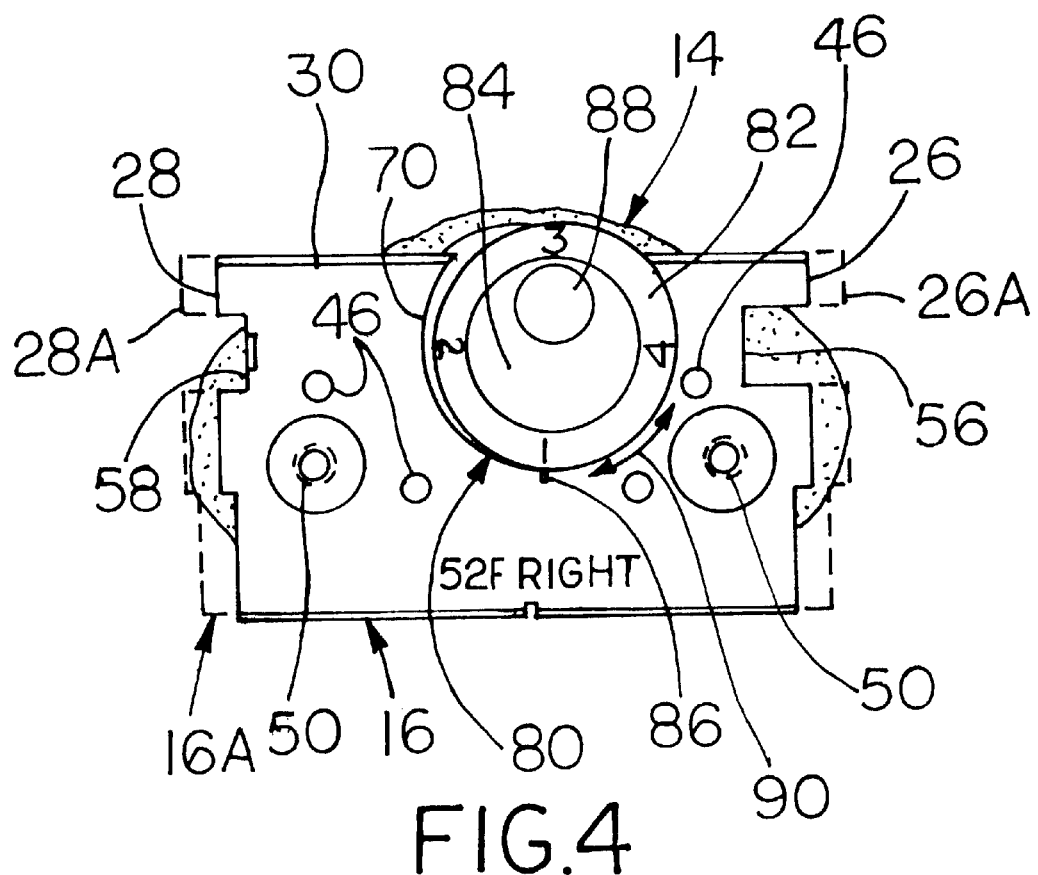
FIG. 4 is a front view of the cutting guide block attached to a femur, with an embodiment of an offset guide bushing disposed within an opening in the cutting guide block.

Referring now to FIG. 4, another embodiment of a bushing 80 which may be utilized with cutting guide block 16 is shown. Bushing 80 is not keyed with cutting guide block 16, and is rotatable relative to cutting guide block 16 when disposed within opening 70 (as indicated by double headed arrow 90). Bushing 80 includes a shoulder 82 and an extension 84, similar to bushing 24 shown in FIG. 5. However, since bushing 80 is rotatable within cutting guide block 16, shoulder 82 includes visual indicia, referenced 1–4, which allow the angular orientation of bushing 80 to be determined relative to cutting guide block 16. More particularly, a hash mark 86 or other visual indicia on cutting guide block 16 is aligned with a relative position of at least one visual indicia 1–4. Bushing 80 includes an offset opening 88 which is disposed offset relative to a longitudinal axis (not numbered) of bushing 80. The position of a visual indicia 1–4 relative to hash mark 86 thus provides an indication of the orientation of opening 88 relative to the longitudinal axis of bushing 80. This rotational orientation corresponds to the orientation of an offset stem of an implant in the event that the intramedullary canal within femur 14 requires the use of such an offset stem.

During use, epicondylar alignment guide 18 is detachably connected with cutting guide block 16, and abutment surface 34 is placed against the distal end of a right hand femur 14. The size of an implant to be implanted within femur 14 is determined by comparing the width of cutting guide block 16 with the distal end of the femur. After placing a proper size cutting guide block 16 against the distal end of femur 14 and aligning epicondylar alignment guide 18 relative to the epicondyles of femur 14, cutting guide block 16 is pinned to the distal end of femur 14 using bone pins 48 extending through selected pin holes 46. The surfaces of femur 14 may be shaped by placing saw blade 38 flat against anterior cutting guide surface 30A or posterior cutting guide surface 32. To assist in maintaining saw blade 38 at a predetermined angular orientation relative to posterior cutting guide surface 32, posterior saw guide 20 may be detachably connected to cutting guide block 16 at posterior cutting guide surface 32. Posterior saw guide 20 is then removed and anterior flange 22 is attached to the selected cutting guide block 16. After arms 66 of anterior flange 22 are received within the corresponding notches 56 and 58 of cutting guide block 16, thumb screw 68 is tightened to inhibit relative movement therebetween. Additional bone pins 48 may be inserted into femur 14 through pin holes 49. A bushing 24 having an opening 72 with a selected inside diameter is placed within opening 70 of cutting guide block 16. A drill bit 78 or a reamer with an outside diameter corresponding to the inside diameter of opening 72 is passed through bushing 24 and into femur 14. The inside of femur 14 is prepared using drill bits and/or reamers until "chatter" corresponding to the removable of cortical bone is heard. If the intramedullary canal within femur 14 requires the use of an implant with an offset stem, an offset bushing 80 (FIG. 4) may be used to determine the angular orientation of the offset stem of the implant to be implanted within femur 14. After the distal end of femur 14 is prepared, orthopaedic instrumentation 10 is removed and an orthopaedic implant is implanted within the distal end of femur 14 as the femoral component of a knee joint.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. Orthopaedic instrumentation used for preparing a distal end of a femur during an orthopaedic revision surgery, said instrumentation comprising:

a cutting guide block including a medial side, a lateral side and an anterior cutting guide surface, said medial side and said lateral side each having a notch therein; and an anterior flange removably attached to said cutting guide block and positioned adjacent said anterior cutting guide surface, said anterior flange including a pair of arms which are respectively disposed within said medial side notch and said lateral side notch.

2. The orthopaedic instrumentation of claim 1, wherein at least one of said arms includes a thumbscrew which engages one of said medial side and said lateral side within said corresponding notch.

3. The orthopaedic instrumentation of claim 1, wherein said anterior flange includes a generally U-shaped plate with two legs, and wherein each said arm is connected with a corresponding said leg via a respective interconnecting portion.

4. The orthopaedic instrumentation of claim 3, wherein said plate, said interconnecting portions and said arms conjunctively have a U-shape when viewed in a medial/lateral direction.

5. The orthopaedic instrumentation of claim 1, wherein said cutting guide block includes two abutment surfaces on opposite sides thereof, each said abutment surface extending transverse to each of said medial side, said lateral side and said cutting guide surface, either of said abutment surfaces being configured for placement against the distal end of the femur.

6. The orthopaedic instrumentation of claim 5, wherein said anterior cutting guide surface includes two cutting guide surfaces, each said cutting guide surface being disposed relative to a corresponding said abutment surface.

7. The orthopaedic instrumentation of claim 6, wherein said cutting guide surfaces are disposed at an obtuse angle relative to each other.

8. The orthopaedic instrumentation of claim 1, wherein said cutting guide block guide includes an opening extending transverse to each of said medial side, said lateral side and said cutting guide surface, and further comprising a bushing disposed within said opening.

9. The orthopaedic instrumentation of claim 8, wherein said bushing is a cylindrical offset bushing with a longitudinally extending opening disposed offset from a longitudinal axis of said bushing, said offset bushing being rotatable within said opening.

10. The orthopaedic instrumentation of claim 8, wherein said bushing is a cylindrical bushing with a longitudinally extending opening disposed concentric about a longitudinal axis of said bushing, said offset bushing being keyed with and non-rotatable within said opening.

11. The orthopaedic instrumentation of claim 1, wherein said cutting guide block includes two abutment surfaces on opposite sides thereof, each said abutment surface extending transverse to each of said medial side, said lateral side and said cutting guide surface, either of said abutment surfaces being configured for placement against the distal end of the femur, and wherein said cutting guide block further includes an opening extending between said abutment surfaces, and further comprising a bushing disposed within said opening, said opening configured to position said bushing at one of two different angles relative to said two abutment surfaces, respectively.

12. The orthopaedic instrumentation of claim 1, further comprising a rotational alignment guide removably attached to said cutting guide block.

13. The orthopaedic instrumentation of claim 12, wherein said rotational alignment guide comprises an epicondylar alignment guide.

14. The orthopaedic instrumentation of claim 1, wherein said cutting guide block further includes a posterior cutting guide surface, and further comprising a posterior saw guide removably attached to said cutting block adjacent said posterior cutting guide surface.

15. Orthopaedic instrumentation used for preparing a distal end of a femur during an orthopaedic revision surgery, said instrumentation comprising:

a plurality of cutting guide blocks, each said cutting guide block including a medial side, a lateral side and an anterior cutting guide surface, each said cutting guide having a different width extending between said medial side and said lateral side, each said medial side and each said lateral side also having a notch therein, each said cutting guide block having a distance between said notches which is the same; and an anterior flange removably attached to one of said cutting guide blocks and positioned adjacent to said anterior cutting guide surface, said anterior flange including a pair of arms which are respectively disposed within said medial side notch and said lateral side notch.

16. The orthopaedic instrumentation of claim 15, wherein at least one of said arms includes a thumbscrew which engages one of said medial side and said lateral side within said corresponding notch.

17. The orthopaedic instrumentation of claim 15, wherein said anterior flange includes a generally U-shaped plate with two legs, and wherein each said arm is connected with a corresponding said leg via a respective interconnecting portion.

18. The orthopaedic instrumentation of claim 17, wherein said plate, said interconnecting portions and said arms conjunctively have a U-shape when viewed in a medial/lateral direction.

19. The orthopaedic instrumentation of claim 15, wherein said different widths of said plurality of cutting guide blocks define femoral component sizing guides for determining a size of an implant to be implanted within the femur.

\* \* \* \* \*